United States Patent [19]

Nevel et al.

[11] Patent Number: 5,761,264
[45] Date of Patent: Jun. 2, 1998

[54] METHOD OF AUTOMATICALLY DETERMINING THE NUMBER OF FILAMENTS IN A SYNTHETIC OR SPUN YARN

[75] Inventors: Avishai Nevel, Providence; Kendall W. Gordon, Jr., North Kingston, both of R.I.

[73] Assignee: Lawson-Hemphill, Inc., Central Falls, R.I.

[21] Appl. No.: 758,462

[22] Filed: Dec. 2, 1996

[51] Int. Cl.⁶ .................................................. G06M 7/00
[52] U.S. Cl. ........................................... 377/6; 377/3
[58] Field of Search ................................. 356/238, 242; 377/3, 6, 10

[56] References Cited

U.S. PATENT DOCUMENTS 3,800,160   3/1974   Ishizawa et al. ........................... 377/6

Primary Examiner—Margaret Rose Wambach
Attorney, Agent, or Firm—Brian M. Dingman

[57] ABSTRACT

A method of automatically determining the number of filaments making up a synthetic yarn, or other yarn such as staple natural fibers comprising removing a small cross-section of the yarn to create a plurality of small filament pieces, and automatically counting the small filament pieces to determine the number of filaments in the yarn.

12 Claims, 2 Drawing Sheets

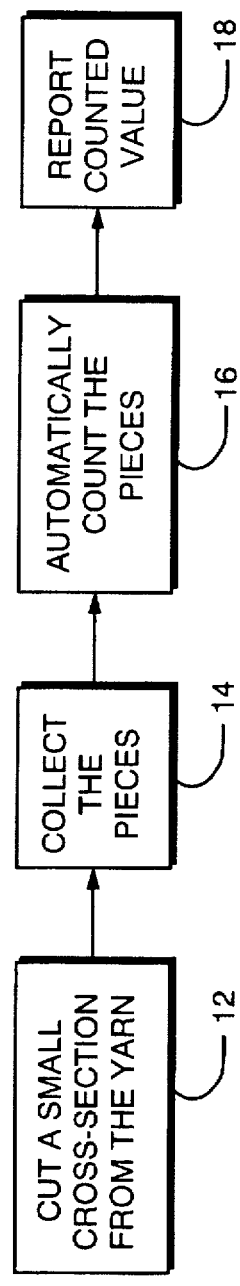
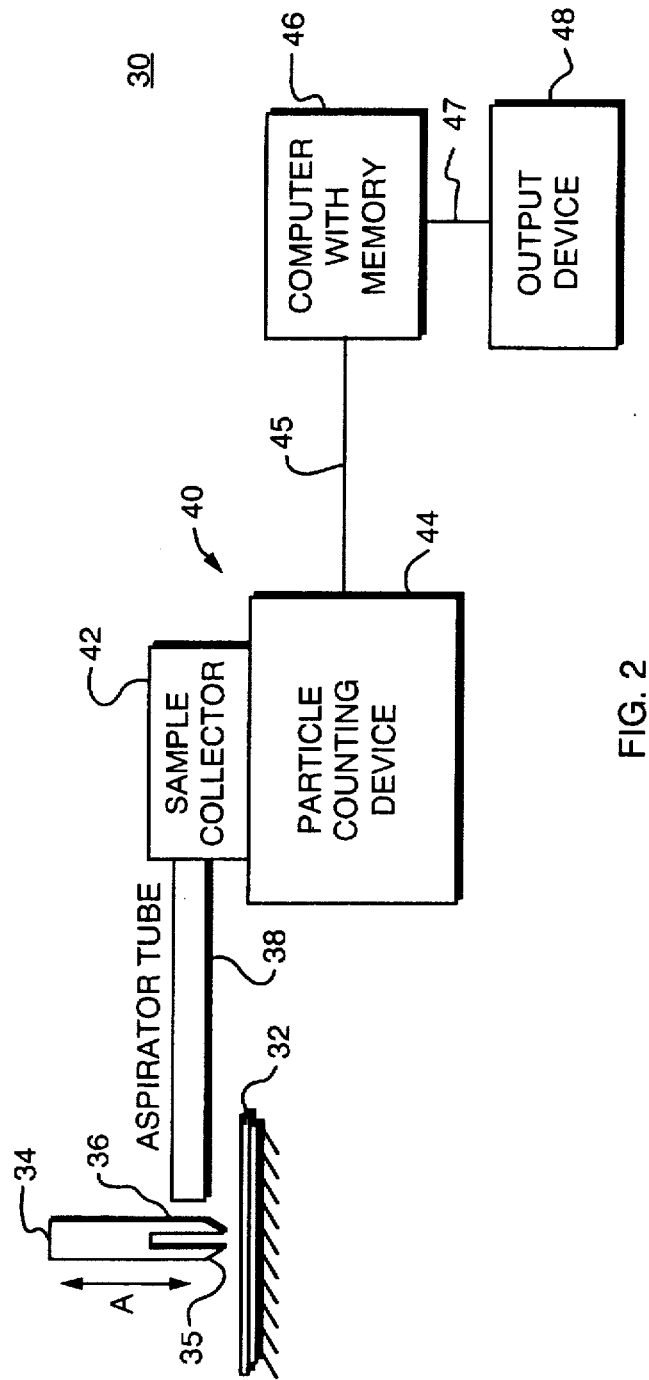

METHOD OF AUTOMATICALLY DETERMINING THE NUMBER OF FILAMENTS IN A SYNTHETIC OR SPUN YARN

FIELD OF INVENTION

This invention relates to a method of automatically determining the number of filaments that make up a multifilament synthetic or natural yarn.

BACKGROUND OF INVENTION

Synthetic yarns are typically made from a number of continuous filaments. For example, a common 70 denier yarn may be made of anywhere from 35 to 200 extremely fine continuous filaments. It is critical to the quality and consistency of the finished product made from such yarns that the yarns be as uniform as possible along their length, which is often measured in kilometers. It is thus necessary for yarn producers and users to be able to determine the number of filaments in the yarn.

Because the filaments are so thin (even less than 0.5 DPF (Den Per Filament)), it has proven to be rather difficult to easily and quickly count the number of filaments in a yarn. This testing is currently accomplished by cleanly slicing the yarn, and inspecting the sliced end either directly using a microscope, or by inspecting an image of the yarn captured with a CCD camera. The number of filaments are then manually counted. This procedure is slow and cumbersome, and can also lead to counting errors due to a number of factors, including operator inattention and lack of expertise, and cutting problems that do not substantially define each separate filament of the yarn. Also, the test is relatively slow and expensive, and thus is not performed as frequently as perhaps it should be. There accordingly is a great need for an improved, automatic filament counting methodology that is simple, inexpensive, reliable, and easy to perform.

SUMMARY OF THE INVENTION

It is therefore an object of this invention to provide a method of automatically determining the number of filaments making up a synthetic yarn.

It is a further object of this invention to provide such a method that does not require operator judgment and is fully automated.

It is a further object of this invention to provide such a method that is quick, simple, and inexpensive to perform.

It is a further object of this invention to provide such a method that is extremely reliable.

This invention features a method of automatically determining the number of filaments making up a synthetic or natural yarn. In one basic embodiment, the method contemplates removing a small cross-section of the yarn to create a number of small filament pieces, and automatically counting those pieces to determine the number of filaments in the yarn.

The cross-section of yarn may be removed by cutting a slice from the yarn. This can be accomplished by tightly holding the yarn very close to the yarn end, and then engaging a cutting edge through the yarn close to the location at which the yarn is held to pass through the yarn. The cross-section can also be removed by cutting through the yarn at two closely-spaced locations, to create a number of small yarn pieces equal to the number of filaments in the yarn, and then collecting the yarn pieces.

The yarn cutting operation may be accomplished by providing a yarn clamping device adapted to firmly grasp the yarn, and engaging the clamping device with the yarn before cutting through the yarn. After the first cut, the yarn can be released from the clamping device and moved in relation to the clamping device, and reengaged with the clamping device before it is again cut through. In this instance, the first cut would be used to square the yarn end, and the second cut would be accomplished very close to the first cut to create a number of uniform, small filament pieces that are amenable to counting by automatic particle counter/analyzer using a laser or other technologies.

The small filament pieces are preferably individually counted by individually passing them by a counting device. This may be accomplished by entraining the pieces in an air stream, and directing the air stream by the counting device. The counting device may be accomplished with a light beam that passes through the air stream, and a scattered light detector for detecting light that is reflected or scattered by the particles entrained in the air stream.

BRIEF DESCRIPTION OF THE DRAWINGS

Other objects, features and advantages will occur to those skilled in the art from the following description of preferred embodiments, and the accompanying drawings, in which:

FIG. 1 is a block diagram of a basic method according to this invention;

FIG. 2 is a simplified schematic diagram of one form of an apparatus that can be used to accomplish the method of FIG. 1;

DESCRIPTION OF THE PREFERRED EMBODIMENTS

Figure 3:
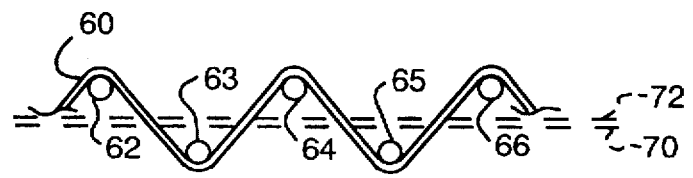
FIG. 3 is a top view of an alternative manner of simultaneously cutting a number of cross-sections from a yarn sample, for use in the methods of this invention.

This invention is accomplished by various methods of automatically determining the number of filaments making up a synthetic or natural yarn. Most basically, the method contemplates first removing a small cross-section of the yarn. Because each of the filaments can have a very small diameter, typically from 8 to 20 micrometers, this creates a number of minute filament pieces. If the cutting is carefully accomplished, the number of pieces is equal to the number of filaments in the yarn. The pieces are then automatically counted by any appropriate particle-counting technology, as a means of determining the number of filaments in the yarn.

To account for error due to cutting, handling or counting problems, more than one such cross-section may be taken and counted, and the number of filaments determined from the largest statistically correct particle count.

There is shown in FIG. 1 in block diagram form method 10 according to this invention. Method 10 contemplates cutting a small cross-section from the yarn, step 12, collecting the pieces, step 14, automatically counting the pieces, step 16, and reporting the counted value, step 18, as the number of filaments in the yarn under test.

This invention contemplates any method of cutting a cross-section from the yarn and automatically counting the small filament pieces thus created. One manner of counting the pieces is with automatic particle counting/analysis equipment, such as the AEROSIZER line of particle analyzers available from Amherst Process Instruments, Inc., Hadley, Mass. The AEROSIZER product is capable of determining the sizes of particles—one by one, at speeds of up to 100,000 particles per second with better than 1% accuracy. The AEROSIZER instruments are capable of measuring particle size, and counting the number of such particles, with sizes at least from 0.2 to 200 microns. The measurement systems use laser beams that traverse an airstream in which the particles to be counted have been entrained, and detect the light scattering created by reflection or diffraction of the light as the particle passes through the light beam. Two spaced laser beams are used to determine the time of flight of each particle. Since the material density is known, this velocity information results in the determination of the particle size.

To accomplish the method of this invention, such equipment need be used only to determine the number of particles. The particle size is relevant only to determine that the size ranges are statistically correct, unless filament denier is also determined. Thus, only one laser beam is necessary to count particles. As the particles move through the laser beam, each burst of scattered light will correspond to a single particle passing through the beam. These instruments can accordingly be used to count the number of small filament particles, and calculate the average filament denier based on particle size and density, if desired. Two laser beams could be used to separately count the number of particles, to increase the particle count accuracy.

To accomplish the desired accuracy, it is necessary to create particles of approximately the same size. This is preferably accomplished by cutting the yarn twice. Both cuts may be accomplished at once as depicted in FIGS. 2 and 3. Alternatively, the cuts can be accomplished sequentially, with relative movement of the yarn and cutter. In either case, the equipment is designed to repeatably cut very small cross-sections of the yarn, and move the small filament pieces from the cutter to the measurement device.

One system for accomplishing these functions is depicted schematically in FIG. 2. System 30 includes closely-spaced cutter blades 35 and 36 that depend from block 34 that is moved up and down in the direction of arrow A to simultaneously make two cuts through yarn 32. This creates a number of small filament pieces, equal in number to the number of filaments making up yarn 32. These pieces are picked up in aspirator tube 38, which entrains them in a flow of air and provides them to sample collector 42 and particle counting device 44 that together make up filament piece counter 40. Counter 40 may comprise an appropriate model of the previously-mentioned AEROSIZER equipment.

The signal representing the particle count is then provided through line 45 to personal computer with memory 46, that stores the count. The computer allows a number of counts to be stored and analyzed, for one or more yarn samples. This allows more than one measurement to be made on each yarn sample, with statistical analysis of the results to determine the number of particles, and thus the number of filaments. Output device 48 (printer and/or CRT) provides information to the operator. Alternatively, device 48 may comprise any other equipment that may use the filament count information.

If the yarn filaments are straight and consistent, and the cut is made entirely through the yarn, and each particle is counted, then the particle count will exactly correspond to the yarn filament count. However, the very small filament pieces will tend to adhere to one another and to surfaces, creating the possibility of a count smaller than the actual number of filaments. Such error can be reduced by careful handling, and also by counting multiple cross-sections, with a report of the largest statistically-correct count. Since the AEROSIZER equipment can also determine particle size, filament piece clumping can actually be detected by an analysis of the particle size distribution, and/or by an analysis of particle mass, since clumped particles will have a mass that is an integral multiple of the mass of individual particles. Clumping can thus be measured, and accounted for in the end result.

If multiple samples are to be created and counted from a single yarn sample, it may be desirable to simultaneously cut multiple cross-sections from a yarn. This can be accomplished as shown in FIG. 3. Yarn 60 is wound around stays 62 through 66, pulled taut, and then simultaneously cut through at two closely-spaced locations with elongated cutting blades 70 and 72. There are numerous additional possibilities for simultaneously cutting a number of small cross-sections from a yarn sample.

Figure 4:
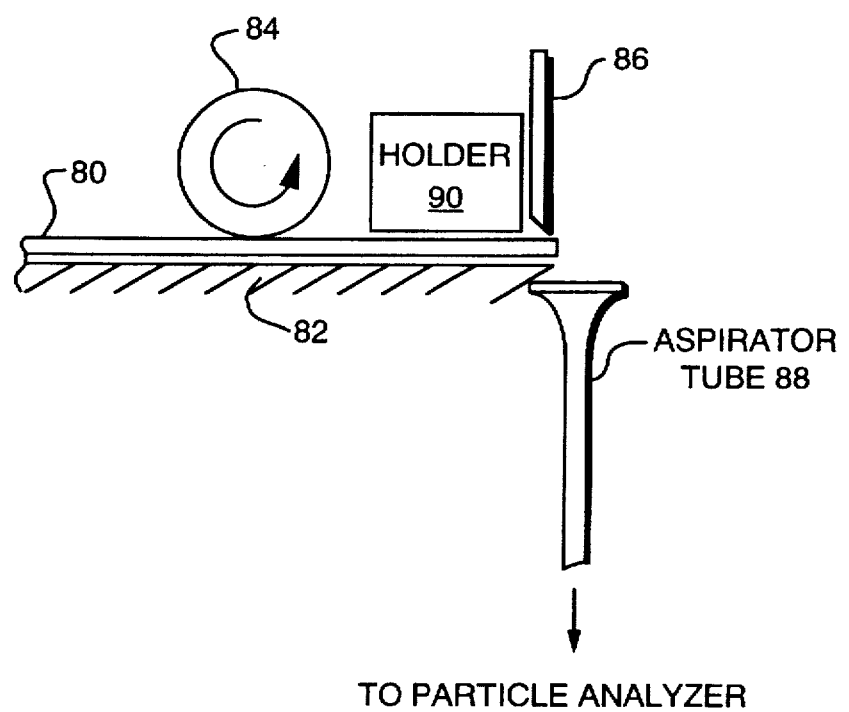
FIG. 4 is a simplified schematic diagram of an alternative apparatus for cutting a cross-section from the yarn to be analyzed.

FIG. 4 schematically depicts an alternative apparatus for cutting a small cross-section from yarn. This apparatus accomplishes sequential cutting of a yarn with a single cutter. Blade 86 is adapted to engage and disengage yarn 80 that is moved along support surface 82 by yarn indexing device 84, which may comprise a roller or other type of clamping mechanism that is adapted to move yarn 80 in small increments. Separate yarn holding device 90 may be used to clamp yarn 80 very close to the location at which it is sliced by cutter 86. Enlarged-end aspirator tube 88 is placed to capture the small filament pieces created when the yarn is cut.

Small cross-sections of consistent length can be cut by the apparatus of FIG. 4 as follows. Yarn 80 would be advanced by mechanism 84, clamped by holder 90 and then cut off by blade 86. This would square the yarn end. Blade 86 and holder 90 would then be disengaged from yarn 80, and device 84 would be indexed to move yarn 80 a very small distance towards cutter 86. Holder 90 would then be engaged, and cutter 86 engaged to remove a small cross-section from yarn 80. Aspirator tube 88 would then move the particles to the particle analyzer as described above.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A method of automatically determining the number of filaments making up a yarn, comprising:
   a. removing a small cross-section of the yarn to create a first plurality of small filament pieces; and
   b. automatically counting the first plurality of small filament pieces to determine the number of filaments in the yarn.

2. The method of claim 1 in which removing a small cross-section of yarn includes cutting a slice from the yarn.

3. The method of claim 2 in which cutting a slice from the yarn includes tightly holding the yarn very close to the yarn end, and then engaging a cutting device to cut the yarn close to the location at which the yarn is held.

4. The method of claim 1 in which removing a small cross-section of yarn includes cutting through the yarn at a first location along the yarn, and cutting through the yarn at a second location very close to said first location to produce a number of very small yarn filament pieces essentially equal in number to the number of filaments, and collecting said yarn filament pieces.

5. The method of claim 4 in which removing a small cross-section of yarn further includes providing a yarn clamping device adapted to firmly grasp the yarn, and engaging said clamping device with the yarn before cutting through the yarn at a first location.

6. The method of claim 5 in which removing a small cross-section of yarn further includes releasing the yarn from said clamping device after cutting through the yarn at a first location, moving the yarn in relation to said clamping device, and again engaging said clamping device with the yarn before again cutting through the yarn at a second location very close to the first location.

7. The method of claim 1 in which automatically counting the small filament pieces includes individually counting the pieces.

8. The method of claim 7 in which individually counting the pieces includes individually passing the pieces by a counting device.

9. The method of claim 8 in which individually passing the pieces by a counting device includes entraining the pieces in an air stream, and directing the air stream by said counting device.

10. The method of claim 9 in which said counting device includes a light beam passing through said air stream, and means for detecting reflectance of said light beam from said pieces entrained in said air stream.

11. The method of claim 1 further including the steps of:

c. removing a further small cross-section of the yarn to create a further plurality of small filament pieces;

d. automatically counting said further plurality of small filament pieces;

e. repeating steps c and d one or more times;

f. comparing the counts; and g. reporting the largest statistically correct count as the determined number of filaments in the yarn.

12. A method of automatically determining the number of filaments making up a synthetic yarn using a computer memory, comprising:

a. cutting a small cross-section of the yarn to create a plurality of small filament pieces;

b. collecting the plurality of small filament pieces;

c. automatically counting the collected filament pieces;

d. storing the count from step c. in computer memory;

e. repeating steps a through d one or more times on the same yarn;

f. comparing the counts stored in the computer memory and finding the largest count; and g. reporting the largest count as the determined number of filaments in the yarn.

* * * * *